US00PP12995P2

(12) United States Plant Patent
Zary

(10) Patent No.: US PP12,995 P2
(45) Date of Patent: Sep. 24, 2002

(54) MINIATURE ROSE PLANT NAMED 'JACENRAM'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 17 days.

(21) Appl. No.: 09/724,683

(22) Filed: Nov. 28, 2000

(51) Int. Cl.[7] ..... A01H 5/00
(52) U.S. Cl. ..... Plt./129
(58) Field of Search ..... Plt./116, 123, 122, Plt./129, 150, 151, 141, 142, 143

*Primary Examiner*—Howard J. Locker
(74) *Attorney, Agent, or Firm*—Klarquist Sparkman, LLP

(57) ABSTRACT

Miniature rose plant having thirty or more flowers per flowering shoot; strong fragrance; disease resistant foliage; ability to own root successfully as a hardwood or softwood cutting; and compact, rounded plant habit.

1 Drawing Sheet

The present invention relates to a new and distinct variety of rose plant of the miniature class which was originated by me by crossing the variety La Marne, (not patented) with an unnamed variety whose parents were unnamed varieties.

The primary objective of this breeding was to produce a new rose variety having the vigorous growth, rounded plant habit and disease resistance of the female parent combined with the flower fragrance, compact habit and high flower count per cluster of the male parent. The objective was substantially achieved, along with other desirable improvements, as evidenced by the following unique combination of characteristics that are outstanding in the new variety and that distinguish it from its parents, as well as from all other varieties of which I am aware:

1. Thirty or more flowers pet flowering shoot;
2. Strong flower fragrance;
3. Disease resistant foliage;
4. Ability to own root successfully as a hardwood or softwood cutting; and
5. Compact, rounded plant habit.

Asexual reproduction of this new variety by cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:
*Seed parent.*—La Marne (Not patented).
*Pollen parent.*—Unnamed Seedling.
Classification:
*Botanical.*—*Rosa hybrida.*
*Commercial.*—Miniature.

FLOWER

Observations made from specimens grown in a garden environment at Somis, Calif. in February, 1999–November, 2000.

Blooming habit: Continuous.

Bud:

*Size.*—About ⅜ inch long when the petals start to unfurl.

*Form.*—The bud form is short, pointed ovoid.

*Color.*—When sepals first divide, bud color is Red Group 53D. When half blown, the upper sides of the petals are Red Group 53B; and the lower sides of the petals are Red Group 53D.

*Sepals.*—Color: Green Group 138B. Surface texture: Covered in fine hairs. There are three lightly appendaged sepals. There are two unappendaged sepals with hairy edges.

*Receptacle.*—Color: Green Group 137C. Shape: Funnel. Size: Small, about 3/16"×1/8". Surface: Hairy.

*Peduncle.*—Length: Short, averaging about 1¼ inches. Surface: Covered in fine hairs. Color: Green Group 138C except when exposed to bright sunlight. Then it is Greyed-Red Group 181B. Strength: Bending, slender.

Bloom:

*Size.*—Small. Average open size is 2 inches.

*Borne.*—Several together, in pyramidal clusters of up to 30 blooms.

*Stems.*—Strength: Strong. Average length is about 12–14 inches.

*Form.*—When first open: Bloom is cupped. Permanence: Flattens, outer petals curl back.

*Petalage.*—Number of petals under normal conditions: 20.

*Color.*—The upper sides of the petals are Red Group 53B. The open flower has some petals with a white streak of white group 155D on the mid-rib. The reverse sides of the petals are Red Group 53D. The base of each petal has on the upper surface a large Yellow Group 4D colorspot ⅜"×⅜" with a 1/16"×1/16" Yellow Group 4C area at the point of attachment. The lower surface has 3/16"×3/16" Yellow Group 4D colorspot. The major color on the upper side is Red Group 53B.

*Variegations.*—There are occasional White Group 155B streaks on the upper surface of the petals and lighter colored mid-ribs on the lower surface.

*Discoloration.*—The general tonality at the end of the first day: No change. At the end of the third day: Fading to Red Group 53D and by day five fading to near white on the petal edges. Petals fall on day six.

*Fragrance.*—Strong, hyacinth.

Petals:

*Texture.*—Thin.

*Shape.*—Oval to deltoid to spatulate.

*Form.*—Tips slightly recurved.

*Arrangement.*—Imbricated. Petaloids in the center are few and small. Similar in color to the petals and number two or three per flower. Vary in size ¼"×⅛" to ⅓"×⅛".

*Persistence.*—Petals drop off cleanly before drying.

*Lastingness.*—On the plant: Short (about 5–6 days). As a cut flower: Short (about 5–6 days).

Reproductive parts:

*Anthers.*—Size: Medium. Quantity: Many. Color: Yellow-Orange Group 22B. Arrangement: Regular around styles.

*Filaments.*—Color: Yellow Group 5C.

*Pollen.*—Color: Yellow-Orange Group 17A. The pollen is fertile. There is almost no natural hip set. However, hand pollination with the pollen of other rose plants has been successful.

*Styles.*—Color: Yellow-GreenGroup 1A.

*Stigmas.*—Color: Green-White Group 157C.

Plant:

*Form.*—Bush.

*Growth.*—Vigorous, branching and compact. At maturity, (one full growing season) height is 2½ feet, width is 2 feet.

Foliage:

*Number of leaflets on normal mid-stem leaves.*—7.

*Size.*—Long, narrow (5–6 inches long×3½–4 inches wide).

Quantity:

*Color.*—New foliage: Upper surface: Greyed-Orange Group 176A. Lower surface: Greyed-Orange Group 176A. Old foliage: Upper surface: Green Group 137A.

Leaflets.

*Shape.*—Pointed oval.

*Texture.*—Leathery, glossy.

*Edge.*—Serrated.

*Serration.*—Single, small.

*Petiole rachis.*—Color: Green Group 137C.

*Petiole underside.*—Rough, with prickles.

*Stipules.*—Medium, serrated (about ½ inch long, bearded and with glands).

*Disease resistance.*—Resistant to mildew and rust, susceptible to blackspot under normal growing conditions.

Wood:

*New wood.*—Color: Greyed-Red Group 178A. Bark: Smooth.

*Old wood.*—Color: Green Group 137C. Bark: Smooth.

Prickles:

*Quantity.*—On main canes from base: Ordinary. On laterals from main canes: Ordinary.

*Form.*—Medium, hooked downward.

*Color when young.*—Greyed-Purple Group 184A.

*Color when mature.*—Greyed-Orange Group 177A.

Small prickles:

*Quantity.*—On main stalks: None. On laterals: None.

I claim:

1. A new and distinct variety of rose plant of the miniature class, substantially as herein shown and described, characterized particularly by its thirty or more flowers per flowering shoot; strong fragrance; disease resistant foliage; ability to own root successfully as a hardwood or softwood cutting; and compact, rounded plant habit.

* * * * *

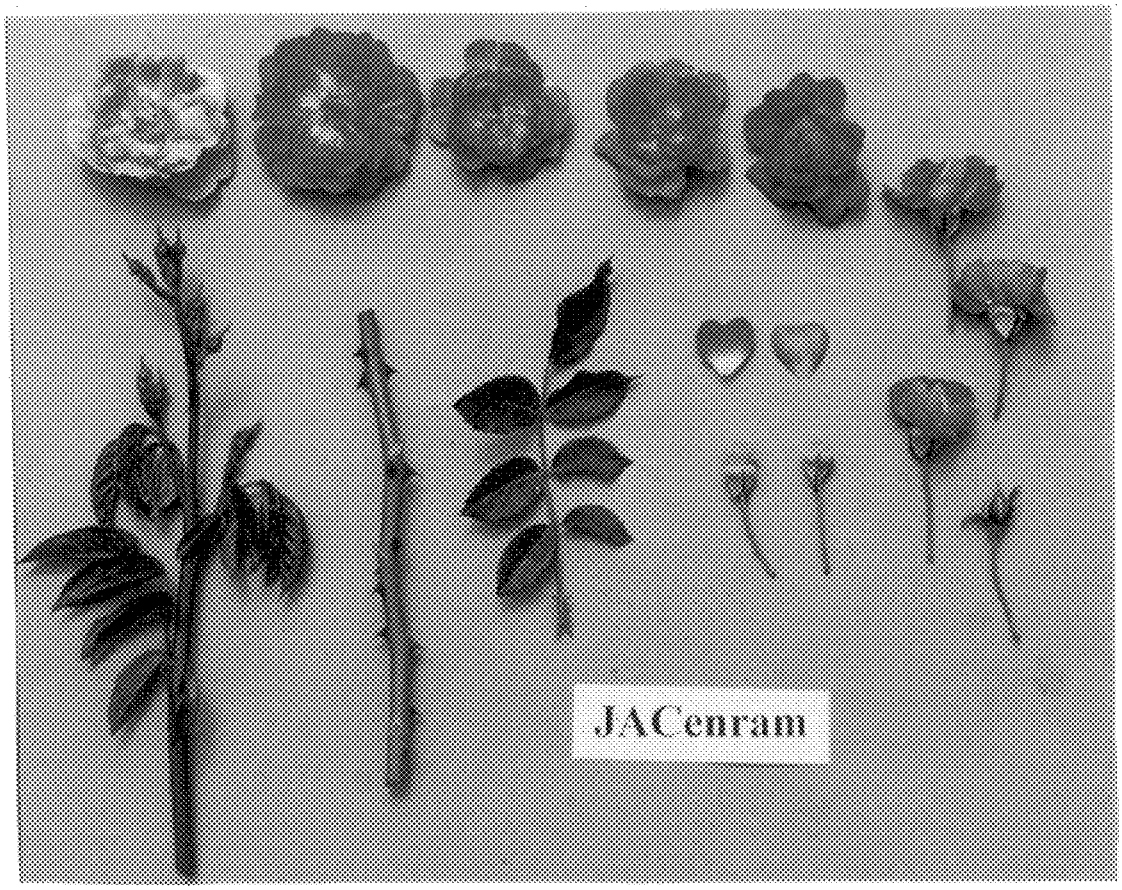
JACenram